United States Patent [19]

Crabtree et al.

[11] Patent Number: 5,104,503

[45] Date of Patent: * Apr. 14, 1992

[54] PHOTOCHEMICAL DIMERIZATION OF ORGANIC COMPOUNDS

[75] Inventors: Robert H. Crabtree, Bethany, Conn.; Stephen H. Brown, Princeton, N.J.; Cesar A. Muedas, New Haven; Richard R. Ferguson, Branford, both of Conn.

[73] Assignee: Yale University, New Haven, Conn.

[*] Notice: The portion of the term of this patent subsequent to Feb. 6, 2005 has been disclaimed.

[21] Appl. No.: 336,376

[22] Filed: Apr. 11, 1989

[51] Int. Cl.$^5$ .......................... C07C 2/76; C07C 29/00; C07F 9/02

[52] U.S. Cl. .............................. 204/157.6; 204/57.63; 204/157.73; 204/157.74; 204/157.81; 204/157.82; 204/157.85; 204/157.92; 204/157.93; 204/157.94; 204/157.95; 204/157.9; 204/158.14

[58] Field of Search ........... 204/157.15, 157.6, 157.69, 204/157.9, 157.63, 157.93, 157.94, 157.95, 157.92, 157.74, 158.14, 157.81, 157.73, 157.87, 157.82, 157.85, 157; 522/170, 66, 28

[56] References Cited

U.S. PATENT DOCUMENTS

| | | | |
|---|---|---|---|
| 1,746,168 | 2/1930 | Taylor | 522/66 |
| 2,640,023 | 5/1953 | Cier | 204/157.15 |
| 2,655,474 | 10/1953 | Schutz | 204/157.15 |
| 2,657,985 | 11/1953 | Schutz | 204/157.15 |
| 2,762,768 | 9/1956 | Cier | 204/157.15 |
| 2,830,016 | 4/1958 | Cier | 204/157.15 |
| 3,371,024 | 2/1968 | Gunning | 204/157.85 |
| 4,725,342 | 2/1988 | Crabtree | 204/157.15 |
| 4,874,488 | 10/1989 | Crabtree | 204/158.14 |

FOREIGN PATENT DOCUMENTS 59-128339 7/1984 Japan .

OTHER PUBLICATIONS

Japio abstract of 59-128339 (Japanese patent).
Derwent abstract of 59-128339.
Grant et al., Chemical Dictionary, p. 609 (1987).
CRC Handbook C-219 (1977).
Steacie, Chem. Revs. 1938, 22, 311.
Cario, Z. Physik, 1922, 11, 1955.
Cvetanovic Adv. Photochem. 1963, 1, 115.
Rabinovitch, Can. J. Chem., 1943, 321, 251.
Dalton, Chapter 3: "Silane Photochemistry," pp. 149-230.
Elad, "Photochemical Additions to Multiple Bonds," pp. 168-213.
Gunning et al., "The Mechanism of Energy Transfer in the Triplet Mercury Photosensitization of Paraffins," Journal of the American Chemical Society 95:3, Feb. 7, 1973, pp. 746-751.
Haszeldine et al., "Polyfluoroalkyl Compounds of Silicon. Part VI. Reaction of 3,3,3-Trifluoropropene with Silane . . . ," Synthesis of Heterocyclic Compounds. Part X, 1965, pp. 2101-2107.
Haszeldine et al., "Kinetics of the Reactions of Silicon Compounds. Part VI. Photolytic Addition of Trimethylsilane to Tetrafluoroethylene," J. Chem. Soc. (B), 1970, pp. 1634-1642.
Larson et al., "Competitive Unimolecular Decomposition of Alkyl Radicals. Tertiary Butyl Rupture," The Journal of Chemical Physics, vol. 52, No. 10, May 15, 1970, pp. 5181-5183.
Olson et al., "The Polymerization and Hydrogenation of Ethylene by Means of Excited Mercury Atoms," Feb. 1926, pp. 389-396.

(List continued on next page.)

Primary Examiner—John Niebling
Assistant Examiner—Steven P. Marquis
Attorney, Agent, or Firm—Millen, White & Zelano

[57] ABSTRACT

At least one of selectivity and reaction rate of photosensitized vapor phase dimerizations, including dehydrodimerizations, hydrodimerizations and cross-dimerizations of saturated and unsaturated organic compounds is improved by conducting the dimerization in the presence of hydrogen or nitrous oxide.

23 Claims, 1 Drawing Sheet

U.S. PATENT DOCUMENTS

Olson et al., "The Hydrogen-Ethylene Reaction in the Presence of Excited Mercury Atoms," Dec. 1927, pp. 3131–3134.

Oref et al., "Unimolecular Decomposition and Intramolecular Energy Relaxation in the Suprahigh-Pressure Region," The Journal of Chemical Physics, vol. 54, No. 2, Jan. 15, 1971, pp. 575–578.

Schiff et al., "The Reactions of H and D Atoms with Cyclic and Paraffin Hydrocarbons," Canadian Journal of Chemistry, vol. 29, No. 1, Jan. 1951, pp. 1–13.

Taylor et al., "The Reactions of Ethylene, Hydrogen and the Saturated Hydrocarbons Under the Influence of Excited Mercury," vol. 51, Oct. 1929, pp. 2922–2936.

White et al., "Reactions of Silane with Unsaturated Hydrocarbons," Aug. 5, 1954, pp. 3897–3902.

Trost et al., "The Reaction of Hydrogen Atoms with the Paraffin Hydrocarbons," The Journal of Chemical Physics, vol. 16, No. 4, Apr. 1948, pp. 361–364.

PHOTOCHEMICAL DIMERIZATION OF ORGANIC COMPOUNDS

This invention was made with Government support under grant number DE-FGO2-84 ER3297 awarded by the Department of Energy. The government has certain rights in the invention.

BACKGROUND OF THE INVENTION

This invention relates to improved methods of photochemical dimerization of organic compounds, and more specifically for the hydrodimerization of simple and functionalized alkenes, the cross-dimerization of saturated compounds with simple and functionalized alkenes, and the dehydrodimerization of saturated compounds.

Mercury photosensitized dehydrodimerization has been known for many years. $^3P_1$ Hg ($=$Hg*), formed by 254 nm irradiation of Hg vapor, attacks a variety of organic compounds to give dehydrodimers (e.g., the dehydrodimer bicyclohexyl can be obtained from two cyclohexane molecules with loss of hydrogen). See Steacie, E. W. R., Chem. Rev. 22, 311, 1938; Cvetanovic, R. J., Progress in Reaction Kinetics 2, pp. 39–77, 1964; Strausz, O. P., Gunning, H. E. JACS 95, 746, 1973. These dehydrodimers are much less volatile than the parent organic compounds and condense. In the condensed phase, they are protected from further attack, and in this way high yields of dehydrodimer can be obtained with high conversion. Only recently has this principle of vapor pressure selectivity been applied to mercury photosensitized dehydrodimerization. See U.S. Pat. No. 4,725,342 (Brown and Crabtree); Brown, S. H., Crabtree, R. H., J. Chem. Ed., 65, 290, 1988 and JACS, 1989 (in press). Quantum yields from 0.1–0.8 were obtained, but certain compounds with strong C—H bonds ($CH_4$, $C_2H_6$,$(CH_3)_3COH$) failed to give products. Such substrates are known to react very inefficiently with $^3P_1$ Hg (see Cvetanovic, 1964, supra).

Many other mercury photosensitized processes have been described for treating organic compounds. U.S. Pat. No. 2,636,854 (Cier) discloses the production of aromatic compounds from alkanes. U.S. Pat. No. 2,640,023 (Cier) discloses the production of branched paraffinic hydrocarbons from a mixture of paraffinic hydrocarbons. U.S. Pat. No. 2,730,495 (Gray) discloses the production of alkyl and cycloalkyl hydroperoxides from a gaseous mixture of oxygen and one or more volatile paraffins or cycloparaffins. U.S. Pat. No. 2,908,622 (Bates) describes the production of formaldehyde from methane.

The mercury photosensitized reaction of hydrogen is a recognized source of hydrogen atoms. See Cario, G., Frank, J., Z. Physik, 11, 155, 1922. These hydrogen atoms can add to olefins to give free radicals which are known to give typical free radical reaction products, including hydrodimers. For example, the hydrodimer $C_4H_{10}$ can be obtained from two ethylene molecules and a hydrogen molecule. See Cvetanovic, R. J., Advances in Photochemistry 1, pp. 115–82, 1963, and E. W. R. Steacie, Chem. Revs., 1938, 22, 311.

The mercury photosensitized reaction of nitrous oxide is a recognized source of oxygen atoms. These can add to unsaturated hydrocarbons or abstract H atoms from saturated hydrocarbons. See Cvetanovic, 1963, supra.

The present invention is the result of continuing investigations in this area in which the effect of carrying out mercury photosensitized reactions of functionalized alkenes in the presence of hydrogen was examined. Physico-chemical studies have involved the use of mercury photosensitization of $H_2$ in the presence of simple lower alkenes, but in the sixty years that this has been known, it has not been considered for preparative work, let alone a candidate for the commercial production of dimers, for several reasons. The literature suggests that (1) fragmentation of the alkene-derived radical is an important side reaction, (2) hydrogenation of the alkene is an important, even a major reaction, (3) only small amounts of material can be treated, (4) expensive apparatus is required, (5) a mixture of products is obtained, and (6) functionalized products cannot be employed.

Concerning reasons (1) and (2), Steacie, the most highly regarded figure in the field, notes in his key review (E. W. R. Steacie, Chem. Revs., 1938, 22, 311) that Olsen and Meyers (J. Amer. Chem. Soc., 1926, 48, 389 and 1927, 49, 3131) observed hydrogenation of ethylene as the major pathway, fragmentation to methane as the next most important pathway, and dimerization as the least important pathway in the presence of excess $H_2$. The only higher boiling products noted by H. S. Taylor and D. G. Hill (J. Amer. Chem. Soc., 1929, 51, 2922) were involatile teleomers of the form $C_nH_{2n}$, which were formed only in low yield. The only recent work in the area was carried out by Rabinovitch (I. Oref, D. Schuetzle, and B. S. Rabinovitch, J. Chem. Phys., 1971, 54, 575), who reported that Cis-2-butene was converted to butane, butene, and isooctanes of undetermined isomer distribution. The only alkenes of six carbons or more, e.g., 2,2,3-trimethylpent-1-ene, on the other hand, gave largely fragmentation to lower boiling species and did not give dimers (C. W. Larson and B. S. Rabinovitch, J. Chem. Phys., 1970, 52, 5181). Based on these reported investigations of mercury photosensitized reactions, one would not suspect that a specific isomer of a dimer could be obtained as the predominant reaction product, or that the reaction could be conducted on commercial scale, or that functionalized alkenes could be used, or that higher alkenes, e.g., with six carbons, or more could be dimerized. In fact, even the apparatus used in our own previous work (U.S. Pat. No. 4,725,342) is not satisfactory for the preparatory methods of this invention, which requires minimum residence time for the reaction products, is not highly selective.

H atoms addition to alkenes is known to produce "hot" (vibrationally excited) alkyl radicals. These are known to decompose more easily than "cold" radicals, and to react with $H_2$ to give the corresponding alkane (B. S. Rabinovitch, S. G. Davis, C. A. Winkler, and Canad. J. Res., 1943, B21, 251). These radicals would be expected to give disproportionate alkane and isomerized alkene, which in turn would be expected to participate in subsequent reactions. Consequently, one would expect to obtain an undesirable mixture of products, even with simpler alkenes and especially so with functionalized alkenes.

U.S. Pat. No. 4,725,342 specifically states that alkenes do not dimerize under the conditions described therein. However, it has now been found that under certain conditions, rapid and efficient dimerization of simple and functionalized alkenes to give specific isomers of the dimer products is possible. Under those conditions, the H atoms selectively add to the alkene to give the more substituted free radical, and so the dimer of this radical is the major product of the reaction.

(1)

(2)

(3)

(4)

The products can be similar to those obtained in the earlier dimerizations, reported by Brown and Crabtree, supra, but there are a number of significant advantages in this method of this invention. First, the selectivity of the process is determined by the alkene isomer employed, so that the product distribution can be in large measure predetermined. Instead of producing the mixture of all possible 2°—2° dehydrodimers which have formed from alkanes (2°—2° dimers are those that can be considered as being formed from the recombination of two 2° radicals) formed from a compound containing a linear aliphatic chain, only a very restricted number of 2°—2° hydrodimers are formed from alkenes which structurally are capable of producing a mixture of hydrodimers. For example, essentially only 5,6-dimethyl decane is produced from 1-hexene. Not only is there an improvement in selectivity (and resultant yield of desired hydrodimer) but one can also use organic compounds as substrates for the reaction which are not effectively dimerized by methods described in the prior art. For example, Brown and Crabtree (J. Chem. Ed., 1988, supra) found that nitriles do not react and that alkenes, aldehydes and esters give complex product mixtures, and Cvetanovic (1963, supra) notes that perfluorinated compounds are essentially unreactive and that epoxides react to give a complex mixture of products. Therefore, an organic chemist would not suspect that the method would work for functionalized alkenes for the reasons (1)-(5) given above and for the following additional reasons: (7) the hydrogen atoms formed from $H_2$ and Hg* should add to the unsaturated functional groups, rather than or as well as add to the C=C double bonds, (8) the functional groups should quench the Hg* and prevent it from breaking the H—H bond of $H_2$, (9) functionalized alkenes, such as acrylonitrile or vinylsilanes, are particularly liable to polymerize, which Rochow observed for vinyl silanes under Hg photosensitization (D. G. White and E. G. Rochow, J. Amer. Chem. Soc., 1954, 76, 3897).

In the method of this invention, X in Formulae 3 and 4 can contain functional groups which would not be tolerated by our patented method ('342) and which would not be expected to survive H atom reactions. For example, esters give a large number of different products under the conditions of the '342 patent, but in accordance with this invention, unsaturated esters give high conversions and yields of the α—α dimers being those which can be considered as being formed from the recombination of two radicals in which the free radical center is α to the X group). A very significant example of the same pathway involves perfluorinated alkenes. The corresponding fluorocarbons are completely inactive under the conditions of the '342 patent, and no ways are know of dimerizing fluorocarbons efficiently.

In contradistinction, perfluorinated alkenes are efficiently dimerized by the instant process.

Although a certain number of photochemical cross-dimerizations involving silanes and alkenes have been described (J. C. Dalton, Organic Photochemistry 1985, 7, 85), these are the only prior art examples of the general class of reaction between alkenes and saturated species described herein. For example, Haszeldine et al. (R. N. Haszeldine, S. Lythgoe, and P. J. Robinson, J. Chem. Soc. (B), 1970, 1634) found that Me$_3$SiH and $F_2C=CF_2$ gave a variety of cross-dimers. It was suspected that Hg photosensitization was involved as a result of contamination of the reactor with Hg vapor. A mixture of products was obtained, such as Me$_3$SiCF$_2$H, Me$_3$SiCF$_2$CF$_2$CF$_2$CF$_2$H, and Me$_3$SiCF$_2$CF$_2$CF$_2$SiMe$_3$. Based on this prior work in which several molecules of unsaturated component were usually incorporated into the products, it would not seem likely that one would be able to obtain clean formation of the simple cross-dimer incorporating one molecule of each component. Furthermore, a chain reaction was assumed (R. N. Haszeldine, M. J. Newlands, and J. B. Plumb, J. Chem. Soc. 1965, 2101). This erroneous assumption would lead one to predict that an isomeric structure for the cross-product opposite to the one found in accordance with this invention and opposite to the one found in genuine chain reactions. For example, Elad (D. Elad, Organic Photochemistry, 1969, 2, 168) found that 1-alkyl trioxanes were formed in his chain reactions involving 1-alkenes and trioxan, whereas 2-alkyltrioxan is obtained by the method of this invention.

Reactions of saturated hydrocarbons with hydrogen atoms has been described. However, instead of obtaining the hydrodimer obtained under the conditions of this invention, previous workers found that methane, formed by fragmentation of the free radicals was a major product. For example, methane formed 90% of the product from cyclopentane (H. I. Schiff and E. W. R. Steacie, Can. J. Chem., 1951, 29, 1), and methane was the only product from ethane (W. R. Trost and E. W. R. Steacie, J. Chem. Phys., 1948, 16, 361).

The dimerization of internal olefins over a promoted BF$_3$ catalyst to yield oils useful as lubricant basestock is described in U.S. Pat. No. 4,319,064.

OBJECTS OF THE INVENTION

It is the object of the invention to provide a method for the photosensitized hydrodimerization of ethylenically unsaturated nitriles, esters, ethers, ketones, epoxides, silanes, amines, phosphines, and partially or completely fluorinated alkenes which is selective for the production of specified isomers.

Another object is to provide an improved process for the photosensitized hydrodimerization of ethylenically unsaturated compounds, including higher alkenes, e.g., of six carbons or more, that will be selective for the formation of a desired isomer or isomers.

Another object is to provide a method for photochemically cross-dimerizing a saturated compound and an ethylenically unsaturated compound that will be selective for the formation of desired isomer or isomers Another object is to provide an improved method for dehydrodimerizing organic compounds.

Another object is to provide a method for improving the selectivity of the photosensitized dehydrodimerization of saturated compounds.

Other objects will become apparent to those skilled in the art to which this invention pertains.

SUMMARY OF THE INVENTION

In its broadest aspect, this invention relates to a method for increasing at least one of the selectivity and reaction rate of a photosensitized dimerization of an organic compound by conducting the dimerization in the presence of either hydrogen or nitrous oxide, and/or under conditions whereby both the desired dimer and the by-products are removed from the reaction zone as they are formed.

More specifically, this invention relates to improvements in a Group IIb photosensitized vapor phase dimerization in which a gaseous mixture of a Group IIB metal and an organic compound is irradiated in a reaction zone with a photosensitizing amount of radiant energy, in which:

(a) a continuous stream of the gaseous mixture is passed in a single pass through the reaction zone at a temperature at which the desired dimer condenses immediately upon the formation thereof and remains condensed while exposed to the radiant energy and both the condensate and the residual vapor phase are concurrently removed from the reaction zone, thereby minimizing secondary reactions between the dimer and itself, the starting organic compound or any by-products of the dimerization reaction; or (b) the gaseous mixture comprises hydrogen and the organic compound is an ethylenically unsaturated compound selected from the group consisting of unsaturated esters, unsaturated ethers, unsaturated ketones, unsaturated epoxides, unsaturated silanes, unsaturated amines, unsaturated phosphines and fluorinated alkenes; or (c) the gaseous mixture comprises hydrogen and two compounds selected from the group consisting of alkenes of at least six carbon atoms, unsaturated nitriles, unsaturated epoxides, unsaturated silanes, unsaturated amines, unsaturated phosphines, and fluorinated alkenes and a continuous stream of the gaseous mixture is passed in a single pass through the reaction zone at a temperature at which the desired dimer condenses immediately upon the formation thereof and remains condensed while exposed to the radiant energy and the residual vapor phase is concurrently removed from the reaction zone, thereby minimizing secondary reactions between the dimer and itself, the starting organic compound or any by-products of the dimerization reaction; or (d) the gaseous mixture comprises nitrous oxide and the organic compound is a saturated compound with thereof and an alkene; or dimerization is a dehydrodimerization or cross-dimerization of alkanes and saturated hydrocarbon compounds bearing a functional group which inactivates the molecule to excited mercury atom mediated photosensitized dimerization, e.g., a member of the group consisting of alkanes, acids, esters, ethers, ketones, epoxides, silanes, amines, phosphines and partially fluorinated alkanes, and mixtures thereof.

In one process aspect, this invention relates to a method for increasing at least one of the selectivity and rate of mercury photosensitized vapor phase hydrodimerization of an unsaturated alkene compound, such as unsaturated nitriles, esters, ethers, ketones, epoxides, silanes, amines, phosphines, partially or completely fluorinated alkenes, and higher alkenes which are structurally capable of disproportionating into a plurality of products which undergo a variety of undesirable secondary reactions, e.g., alkenes preferably of six or more carbon atoms, which comprises conducting the dimerization in an irradiated reaction zone containing an atmosphere of hydrogen, and the unsaturated compound, at a temperature which permits the hydrodimerized product to condense immediately upon formation and remain condensed while exposed to the radiant energy and in a manner whereby the by-products are removed from the reaction zone as they are formed.

In a second process aspect, this invention relates to a method of increasing at least one of the selectivity and rate of a mercury photosensitized vapor phase cross-dimerization of an unsaturated compound (unsaturated component), such as unsaturated nitriles, esters, ethers, ketones, epoxides, silanes, amines, phosphines and partially or completely fluorinated alkenes, or simple alkene of six carbons or more, with an alkane, ether, alcohol, amine, silane, or partially fluorinated alcohol (saturated component), which comprises conducting the cross-dimerization in an irradiated reaction zone containing an atmosphere of a mixture of the vaporized Group IIb metal, the saturated component and the unsaturated component, at a temperature which permits the dimerized products to condense and remain condensed while exposed to the radiant energy and in a manner whereby the by-products are also removed from the reaction zone as they are formed.

In a composition aspect, this invention relates to the novel compounds produced according to the process of the invention.

Figure 1:
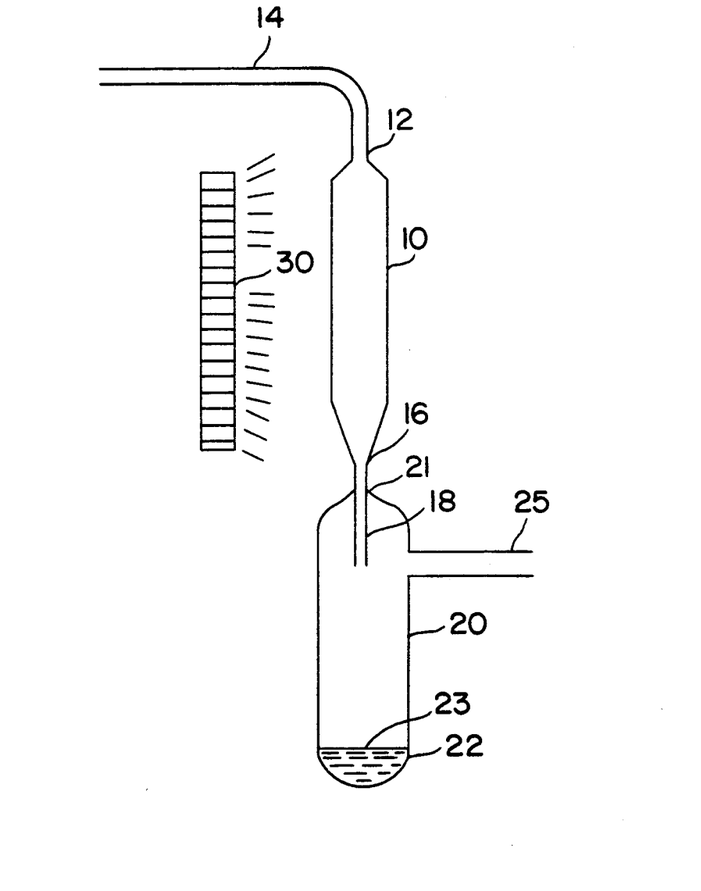
The drawing is a simplified schematic view of the laboratory reactor equipment employed in the examples which follow.

The reactor consisted of a downwardly vertically positioned quartz reactor vessel 10 having an orifice 12 at its upper end forming gas communication with a length of glass tubing 14 sealed to the upper end to collectively form a gas entry port and similar orifice 16 at its lower end providing gas communication with a length of glass tubing 18 similarly sealed to the lower end of the reactor vessel. A product collector is downwardly mounted at its upper end 21 on the second length of glass tubing 18 so that the latter projects downwardly into the interior of the former and provides a narrow gas entry port thereto. The tube diameter is selected so that the gas flow therethrough is sufficient to prevent back diffusion therethrough of gaseous reaction product into the reactor vessel 10. The sealed lower end 23 of product collector vessel 20 provides a reservoir for condensed reaction product 23. Sealed to the upper portion of product collector vessel 20 proximate the terminal free end of glass tubing 18 is a third length of glass tubing 25 which provides a gas exit port from product collector vessel 20. A bank of mercury vapor lamps 30 are positioned proximate the quartz reactor vessel 10. The former can optionally be provided with cooling means (not shown) to prevent emission line broadening and resultant reduction in the quantum yield resulting from excessive heating and the latter optionally can be provided with heating or cooling means (not shown), which does not block the radiation from the lamps 30, to regulate the temperature of the gases in the reactor vessel 10. Similarly, the product collector vessel optionally can be surrounded by cooling means (not shown) to regulate the temperature of the gases therein.

DETAILED DISCUSSION

U.S. Pat. No. 4,725,325 teaches that the tertiary-tertiary selectivity of the photochemical dehydrodimerization of alkanes disclosed therein can be enhanced by conducting the dimerization in an insert atmosphere, e.g., $N_2$, Ar, Xe, acetonitride and $H_2O$.

However, the method of carrying out dehydrodimerizations under $H_2$ or $N_2O$ was not thereby rendered obvious because neither $H_2$ nor $N_2O$ is an inert diluent gas. $H_2$ reacts with Hg* to give H atoms, a fact first reported by G. Cario and J. Frank, Z. Physik, 1922, 11, 155, and used in many investigations since then. These H atoms could reasonably have been expected to add to the intermediate radicals R produced by the excited Hg from the starting alkane RH to yield back the starting alkane. It is not clear why this does not happen.

For saturated substrates which are dehydrodimerized under the conditions of the '342 patent, the addition of hydrogen improves the selectivity. For example, in the case of n-butenol, the selectivity for $\alpha$ attack rises from 30% to 90%. For substrates which do not react under the '342 conditions, e.g., esters, the use of $H_2$ is even less obvious. The H atoms could have attached the substrate non-selectively, they could have attached the R or R' or $CO_2$groups of an $R'CO_2R$, and they could have attacked at the R or R' group non-selectively among the carbon chain. The fact that they attack only $\alpha$ to the ester, at the most highly substituted carbon so that using, e.g., a methyl ester (R=Me) and a long chain R', the desired product of attack at the R' is produced, is therefore surprising.

Also, as noted above, Cvetanovic and Steacie describe the hydrodimerization of ethylene in the presence of hydrogen to yield the hydrodimer $C_4H_{10}$. However, for higher alkenes, the H atoms would be expected to abstract an H atom from various C—H bonds, especially from the reactive allylic C—H bonds, in competition with addition to the C=C double bond, and so a complex mixture should be formed. Surprisingly, this is not the case.

Although the photosensitized dehydrodimerization of alkanes ethers and alcohols has long been known in the prior art, the dimerization ordinarily produced a large number of products. In addition, the method was much less efficient or completely ineffective when applied to nitriles, esters, ethers, ketones, epoxides, silanes, amines, phosphines, and partially or completely fluorinated compounds. A few examples of dimerization of simple alkenes using hydrogen and mercury photosensitizers have also been described.

The present method differs from that employed in the prior art in that the dehydrodimerization is carried out in a hydrogen atmosphere using an unsaturated organic compound and the conditions employed are such that the dimer product promptly condenses in the reaction zone and is thereby protected from further attack. In addition, an apparatus is preferably used which minimizes the residence time of the alkene and alkane products obtained as a result of disproportionation of the initially formed radical. If this were not done, these by-products would undergo unselective dimerization and a mixture of dimeric products would be formed. Unexpectedly, under the conditions of this invention, fragmentation of the alkyl radical is a minor pathway, large amounts of material can be treated in inexpensive apparatus on a large scale, and simple mixtures or even a single dimer is the predominant product, even from functionalized alkenes.

This variant of this invention which produces as the primary reaction product a homodimer of two identical moieties derived from two molecules of an unsaturated compound and two hydrogen atoms is called the UU case (unsaturated-unsaturated dimer).

The present invention renders the selective production of dimers containing a variety of functional groups commercially feasible for the first time. Hydrogen atom addition to olefins has been observed in the prior art but only for unfunctionalized olefins and the reaction has not been used on a preparative scale but instead only in physico-chemical investigations (Steacie, 1938; Cvetanovic, 1963, supra). A key feature of the present improvement is that it permits desired isomers to be selectively synthesized. For example, hexane gives all possible 2°—2° dehydrodimers when dimerized according to the process of the '342 patent. In contrast, in accordance with this invention, 1-hexene gives largely 5,6-dimethyldecane, and 3-hexene gives largely 4,5-diethyloctane.

Alkenes are known to add H atoms so as to give the stabler radical (Cvetanovic, 1963, supra) and therefore 2-hexyl would be expected from 1-hexene and 3-hexyl from 3-hexene. These dimerize under the conditions of this invention and do not fragment or undergo H atom addition. Thus, for example, 2-hexene gives a mixture of 5,6-dimethyldecane, 4-ethyl-5-methylnonane and 4,5-diethyloctane. The unavoidable disproportionation of 2-hexyl to give hexane and hex-2-ene also occurs to a substantial extent (ca. 50%). If the reaction were carried out in the manner described in the ('342 patent), both the hexane and hex-2-ene would undergo subsequent unselective dimerization. In order to prevent this, an apparatus as shown schematically in the drawing was devised which promptly removes both the vapor phase and the liquid phase from the irradiated zone of the reactor. The vapor contains much of the hexane and hex-2-ene, but these compounds also dissolve to a substantial extent in the liquid phase. Therefore, the liquid phase must also be removed promptly as it forms.

A second improvement in accordance with this invention involves carrying out a cross-dimerization of the type first described in the '342 patent of Brown and Crabtree, but using unsaturated components in the new apparatus. In the earlier work, a refluxing vapor phase mixture of two different saturated components were irradiated in the presence of mercury vapor. Cross-dimerization was observed, for example, cyclohexane and methanol gave, in addition to bicyclohexyl and ethylene glycol, the cross-dimer cyclohexanemethanol. This is called the SS' case because the dehydrodimers are formed from moieties derived from two different saturated compounds.

The present invention not only makes the production of desired isomers of such cross-dimers possible but also allows the use of functional groups in the unsaturated component that would not be tolerated under the conditions described in the '342 patent. Two distinct variants of the cross-dimerization are possible One called UU' involves radicals derived from H addition to two unsaturated components. Another, called SU, involves a radical derived from H abstraction from an $sp^3$ carbon (which is called the saturated, or S component, even if it contains unsaturation if the unsaturated carbon atoms are not involved in the dimerization, e.g., a ketone can react by breaking a C-H bond $\alpha$ to the keto group) and a second radical formed by H atom addition to the unsaturated, or U component. The H atom required for the addition to the U component will normally come from Hg* splitting the C-H bond of the S component, rather than from $H_2$. Purely as an aid to comprehension, and not as implying any limitation on the scope of the present invention, a mechanism is presented below which accounts for the observed results in each case:

UU′ Case $$Hg \xrightarrow{h\nu} Hg^* \quad (5)$$

$$Hg^* + H_2 = 2H\cdot \quad (6)$$

$$XCH=CH_2 + H\cdot = X-\overset{\cdot}{C}H-CH_3 \quad (7)$$

$$YCH=CH_2 + H\cdot = Y\overset{\cdot}{C}H-CH_3 \quad (8)$$

$$X\overset{\cdot}{C}H-CH_3 + Y\overset{\cdot}{C}H-CH_3 = (CH_3)YHC-CHX(CH_3) \quad (9)$$

$$Hg \xrightarrow{h\nu} Hg^* \quad (10)$$

$$Hg^* + R-H = R\cdot + H\cdot \quad (11)$$

$$XCH=CH_2 + H\cdot = XC\cdot H-CH_3 \quad (12)$$

$$XC\cdot H-CH_3 + R\cdot = R-CHX(CH_3) \quad (13)$$

In the UU′ case, a mixture of two unsaturated organic compounds, denoted as $XCH=CH_2$ and $YCH=CH_2$, in which X and Y are deactivating functional groups, e.g., an ester, ether, keto, epoxy, silano, amino or phosphino group, in eq. 7 and 8, is used together with $H_2$. The products observed are consistent with the addition of H atoms to each of the unsaturated components, followed by statistical recombination of the resulting radicals. In the SU case, the products observed are consistent with the addition of H atoms formed by the reaction of Hg* with the saturated component adding to the unsaturated component, followed by statistical recombination of the resulting organic radicals.

It is not understood why significant products derived from the fragmentation and hydrogenation reactions expected for radicals, especially hot radicals and more especially for functionalized hot radicals, are not seen in the reaction product. One or all of the following reasons may apply: (A) Free radicals are not involved but are trapped by Hg to give HgR intermediates. The weakly bound Hg protects the radicals from unfavorable reactions but allows radical recombinations. If this is so, the fact that the system employed in the present invention runs with much higher Hg pressure than many of the literature examples may be an important factor. (B) The hot radicals are deactivated by collisions with $H_2$ molecules. If this is important, then the fact that one atmosphere total gas pressure is usually employed, rather than the low pressures previously described, may be important. (C) The functional groups stabilize the adjacent radical center by resonance $\pi$-donor effects, and this may inhibit undesired reactions. No functionalized dimerizations have previously been described. (D) The prompt condensation of the reaction products prevents subsequent gas phase reactions which are the true cause of the formation of a mixture of products obtained in the '342 method. This reason suggests that increasing the space velocity of the $H_2$ stream would be a useful variant in controlling these undesired pathways.

The unsaturated component may be chosen in the UU, UU′ and SU cases so that the resulting reaction products are fewer in number than are obtained in the cross-dimerization using only saturated compounds (the SS or SS′ case), as described in the '342 patent. For example, tetrahydrofuran (THF) and hexane give all possible 2°-$\alpha$ dehydrodimers as the major cross-products (2°-$\alpha$ dimers as those that can be considered as being formed from the recombination of a 2° radical with a radical in which the radical center is $\alpha$ to a functional group, in this case the O atom of the THF). In contrast, under the conditions employed in the present invention (the SU case), 1-hexene and THF yield 1-(1-ethylbutyl)tetrahydrofuran as a result of the new C-C bond being formed at the 2-position of the hexyl chain. Similarly, 3-hexene and THF yield 1-(1-methylpentyl)-tetrahydrofuran as a result of the new C—C bond being formed at the 3-position of the hexyl chain. The isomers are consistent with hydrogen atom addition to the unsaturated component being the deciding factor in the product distribution.

If desired, the hydrogen gas required for the UU and UU′ cases can be diluted in an inert carrier with only modest changes in rate, selectivity and conversion. For example, $CO_2$, $N_2$, Ar, and helium can all be used as carrier gases. Other Group IIB metals can also be used to split the hydrogen molecule, but mercury is the element of choice because of the cheapness of the mercury lamp employed as the source 254 mm radiation and the volatility and unreactivity of mercury. The molar ratio of Hg:$H_2$:organic compound is not very critical. Too little Hg would lead to inefficient absorption of light, but the vapor pressure of Hg at ambient temperature is adequate. The hydrogen mole fraction can vary from about 0.9 to $10^{-6}$, but at the extremes of the range, the reaction goes very slowly because of the paucity of $H_2$ (low mole fraction) or of the organic substrate (high mole fraction).

A suitable mole ratio of reagents can be obtained by passing $H_2$ over or through the unsaturated compound (UU case) at a temperature chosen to result in any selected mole fraction of U in the resultant vapor phase up to about 90%, preferably 2-25%. In the UU′ case, the $H_2$ can be passed over or through a mixture of the unsaturated compounds, the liquid mole ratio of U to U′ being selected so as to result in a vapor phase mole ratio of the unsaturated compounds of about 1:1, or any other desired molar ratio, e.g., from 0.01:1 to 100:1.

The use of vapor phase ratios other than 1:1 lead to "vapor pressure biasing". This is useful, for example, in a UU′ case where one of the components, e.g., U′, is much more valuable than the other component, U. With a 1:1 vapor ratio, and assuming equal rates of reaction of H atoms with U and U′, the ratio of the three hydrodimers $U_2$ will be 1:2:1. The desired product UU′ is, therefore, obtained in 50% yield based on the U′ monomer. In contrast, if the vapor phase mole ratio is adjusted to favor U by 9:1, then the expected ratio of the products $U_2$, UU′, and U′$_2$ will be 81:18:1. This implies a yield of the desired product UU′ of 95% based on the U′ monomer. Raoult's Law can be used to estimate the liquid phase mole ratio required to produce a given vapor phase mole ratio. Experimental product ratios closely match the theoretical ones as calculated above. This vapor pressure biasing method can also be used in an SS' case.

The dehydrodimerizaton of saturated compounds proceeds with higher selectivity when carried out under $H_2$. Presumably, this is because the H atom is a more selective H abstraction agent than is Hg*. Methylcyclohexane gives a mixture of dehydrodimers containing 10% 3°—3° dimer under the conditions of the '342 patent. Under $H_2$, a 40% yield of the 3°—3° dimer is obtained. Cyclopentanone reacts to give a complex mixture under the prior art conditions (Brown and Crabtree, JACS, 1989, in press), but in the presence of $H_2$, essentially only 2,2-bis(cyclopentanone) is obtained. Probably this is because Hg* gives facile energy transfer to keto groups and so leads to undesired products, but H atoms only react by H atom abstraction from the α positions of the ketone.

Dehydrodimerization or cross-dehydrodimerization of substrates with strong C—H bonds, such as methane, t-butanol and 2,2,3,3-tetramethylbutane, are very inefficient under the conditions of the Brown and Crabtree '342 patent, supra. If $N_2O$ is present in the vapor phase, the dehydrodimerizations of these substrates proceed with much greater efficiency. This presumably happens because the reaction of Hg* with $N_2O$ gives oxygen atoms which are more active H atom abstractors than is Hg* itself.

The equipment used for the photochemical reaction of this invention can be any in which irradiation of the gas phase can be carried out at a temperature which will allow the product to condense and both the condensate and the vapor phase to be promptly removed from the irradiated zone of the reactor. Typically, $H_2$ (for UU or UU' cases) or an inert carrier gas, such as $N_2$ (for SU cases) is passed through a sample of the liquid reactant(s) contained in a flask exterior to the photoreactor and which also contains a drop of liquid mercury, and then into the photoreactor. If the reagents are relatively volatile or involatile, they may be cooled or heated, respectively, to bring their vapor mole fraction within a convenient range, e.g., 0.01-0.5. A convenient photoreactor, as shown in the drawing, consists of an elongate quartz tube fitted with an entry port for the gas and a device for removing the liquid phase and residual vapor phase continuously therefrom. The product condenses and collects in the lower flask, which is made of a material, such as metal or pyrex glass, which is opaque to 254 nm light, and the gaseous phase of the reaction product is rapidly removed from the quartz tube.

That part of the hydrogen required as a carrier gas but not consumed in the process can be recycled through the apparatus as many times as necessary, However, the uncondensed organic products in admixture therewith must first be condensed so that their presence does not adversely affect the selectivity of the reaction Additional hydrogen must be supplied to make up for the hydrogen consumed and for any adventitious losses In the SU case, nitrogen or some other inert carrier gas, such as $N_2$ or $CO_2$, can be used.

The rate of radiant energy input is the factor that limits the product formation rate. Therefore, for a commercial-scale operation it is important to maximize this rate. At the same time, the emission spectrum of the emitter must closely match the absorption spectrum of the Group IIB absorber. This means that in the case of mercury as the absorber, low pressure mercury lamps should be used so that the emission occurs as a narrow atomic line at 253.7 nm, to match the narrow absorption line of the gas phase mercury atom in the vapor phase in the reactor. Lasers and/or reflectors can be used to increase the radiation level in the reaction zone and/or to reduce the residency time of the gaseous phase in the irradiated zone.

The reaction can be carried out at ambient, reduced or elevated temperature. However, if the temperature is too high, the radicals will fragment, and more complex mixtures will be obtained as reaction product. The limiting temperature is different for each system and can be determined experimentally. It is rare, however, that problems are encountered at <100° C. If the reaction temperature (which always must be high enough to volatilize the reactants) is too low, then insufficient mercury will be present in the vapor to absorb all the light. In the apparatus described herein, the point at which this fall-off in rate is observed lies somewhere below room temperature. Therefore, about 25°-100° C. is a convenient and preferred range for the reaction.

The process can be carried out at ambient, reduced or elevated pressure. The dependence of rate, conversion, and yield on total pressure is not pronounced, the chief effect observed being a fall in reaction rate below about 200mgHg. Atmospheric pressure is a convenient and generally preferred pressure for carrying out the process.

The reactor shown in the drawing is much superior to the one described in the '342 patent for carrying out hydrodimerizations, an example of which is the dehydrodimerization of hexane to a mixture of bihexyls in the old reactor versus hexene-1 hydrodimerization to 2,2'-bihexyl in the new one. In the '342 reactor, the radicals are created by H atom abstraction from hexane at all 2° C—H bonds. The resulting radicals meet and either recombine to give product or disproportionate to give 1-, 2-, and 3-hexenes and hexane. Although the disproportion products also remain in the vapor phase, this is not harmful because the secondary reactions of these products produce the same isomeric mixture as the primary reaction. In contradistinction, in a hydrodimerization of this invention, a single specific radical is formed in the primary reaction by H atom addition to the alkene, e.g., 2-hexyl from 1-hexene. The resulting radicals meet and either recombine to give, in the case of 1-hexene, 2,2'-bihexyl, or disproportionate to give, in the case of 1-hexene, 1- and 2-hexenes and hexane. In this case, secondary reactions of the disproportionated products do not lead to the same product, e.g., 2,2'-bihexyl, as the primary reaction, but instead give an undesired mixture. Therefore, both the vapor phase and the liquid condensate must be removed form the reaction zone as they are formed because both contain a portion of the disproportionation products. Table 1 shows how the ratio of 2°—2° products depends on the type of reaction conducted and on the apparatus used. The '342 reactor was the reflux reactor described in the '342 patent and the "new" reactor was a pass-through reactor, as shown in the drawing.

TABLE 1

Results showing the effect of using the new apparatus and of using $H_2$ on the product distribution of 2'-2' bihexylis.

| Substrate | Reactor | 2.2' | 2.3' | 3.3' |
|---|---|---|---|---|
| hexane | '342 | 26 | 51 | 25 |
| hexane/$H_2$ | '342 | 25 | 50 | 25 |
| hexane/$H_2$ | new | 25 | 50 | 25 |
| 1-hexene | '342 | trace | trace | trace |
| 1-hexene/$H_2$ | '342 | 65 | 31 | 4 |

TABLE 1-continued

Results showing the effect of using the new apparatus and of using $H_2$ on the product distribution of 2°-2° bihexylis.

| Substrate | Reactor | 2.2' | 2.3' | 3.3' |
|---|---|---|---|---|
| 1-hexene/$H_2$ | new | 96 | 3.5 | 0.5 |

A mixture of d,l and meso compounds are formed in about 1:1 molar ratio where the structure of the compound allows the production of such isomeric forms. The meso compound can often be departed by crystallization or by gas or liquid chromatography.

Examples of specific reactions that can be carried out by this process in the presence of hydrogen and the yield of the products produced are:

|  | Major product(s) |
|---|---|
| Alkene/alkene | |
| 1-hexene | 5,6-dimethyldecane (72%) |
| 2-hexene | 5,6-dimethyldecane (23%) |
|  | 5-methyl-6-ethylnonane (45%) |
|  | 4,5-diethyloctane (21%) |
| 3-hexene | 4,5-diethyloctane (68%) |
|  | 5-ethyl-6-methylnonane (11%) |
| Fluoroalkene/fluoroalkene | |
| Perfluoro-1-heptene | 6,7-bis(difluoromethyl)per- fluorodecane (55% |
| Alcohol/alcohol | |
| 4-pentenol | 4,5-dimethyloctane-1,8-diol (68%) |
| 3-methyl-3-buten-1-ol | 3,3,4,4-tetramethylhexane-1,6-diol (77%) |
| Cyclohexanone | 2,2'-Bis(cyclopentanone) |
| Amine/amine | |
| Allylamine | 2,3-dimethylbutane-1,4-diamine (70%) |
| Silane/silane | |
| Allyltriethylsilane | 2,3-dimethyl-1,4-bis(trimethylsilyl)-butane (84%) |
| 5,6-epoxy-1-hexene | 1,2,9,10-bis(epoxy)-5,6-dimethyldecane (66%) |
| Ketone/ketone | |
| Hex-1-ene-5-one | 5,6-dimethyldecane-2,9-dione (74%) |
| 2-methylpent-1-ene-4-one | 4,4,5,5-tetramethyloctane-2,7-dione (55%) |
| Nitrile/nitrile | |
| 2-cyanopropene | 1,2-dicyano-1,1,2,2-tetramethylethane (94%) |
| Ester/ester | |
| 2-acetoxypropene | 1,2-diacetoxy-1,1,2,2-tetramethylethane (92%) |
| 3-acetoxypropene | 1,4-diacetoxy-2,3-dimethylbutane (50%) |
| Methyl acrylate | 2,3-di(carboxymethyl)butane (82%) |
| Ether/ether | |
| allyl ethyl ether | 2,3-diethoxybutane (81%) |
| Phosphine/phosphine | |
| trivinylphosphine | 2,3-bis(diallylphosphino)butane (81%) |

Certain SS or SS' dehydrodimerizations are very inefficient or do not occur at all under the conditions of the '342 patent, for one of two reasons: The Hg* may undergo energy transfer to a group present in the substrate without leading to C—H bond breaking. This is the case for ketones. Running the reaction in the presence of $H_2$ leads to the formation of H atoms which are unaffected by the presence of the keto group and abstract the α-C-H hydrogen atom and lead to the α—α dimer. A second reason for failure is that the C—H bonds of some compounds are too strong to be broken easily by the Hg*, which is the case for methane, 2,2,3,3-tetramethylbutane, and t-butanol. In such cases, $N_2O$ renders the reaction operable. The probable reason is that Hg* reacts with $N_2O$ to give an oxygen atom, which is a more active H-abstractor than Hg* or H atoms. The resulting radicals smoothly dimerize.

Examples of substrates which are efficiently dehydrodimerized or cross-dimerized in the presence of $H_2$ or $N_2O$ are shown below.

| Alkane/alkane | |
|---|---|
| 2,2,3,3-tetramethylbutane | 2,2,3,3,6,6,7,7-octamethyl-octane ($N_2O$) |
| Alcohol/alcohol | |
| t-Butanol | 2,2,5,5-tetramethyl-2,5-hexanediol |
| Alkane/alcohol | |
| Methane + methanol | Ethanol ($N_2O$) |
| Ketone/ketone | |
| Cyclopentanone | Bicyclohexyl-2,2'-dione($H_2$) |
| Ester/ester | |
| Methyl propionate | 2,3-dimethylsuccinic acid dimethyl ester ($H_2$) |
| Methyl isobutyrate | 2,2,3,3-tetramethylsuccinic acid dimethyl ester ($H_2$) |
| Carboxylic acid/acid | |
| Propionic acid | 2,3-dimethylsuccinic acid ($H_2$) |

The products of the reactions of this invention are useful for purposes which are self-evident from their structure. For example, the fluorinated materials are useful waxes, the diols are emollients and monomers for polyesters, the diepoxides are cross-linking agents for a variety of resins, the diamines are useful monomers for polyamides, the dinitriles are useful precursors to the corresponding diamines, which are also useful as monomers, the phosphine is a chelating ligand for use in homogenous catalysts. Some of the products are novel compounds because of the great difficulty of preparing them by any other route, for example, the phosphine and fluoroalkene dimers.

The preferred starting compounds have boiling points from 20 to 200° C, more preferably 25 to 150° C, at atmospheric pressure, e.g., alkanes, including cycloalkanes, alkenes, including cycloalkenes, alkanes bearing an inactivating functional group as defined herein and alkenes bearing an X or Y group, e.g., saturated alkane carboxylic acids and esters.

Contemplated equivalents of the functional X or Y groups are amide, sulfoxide, sulfone, carboxyl, and fluoroalkyl, and contemplated equivalents of the ethylenically unsaturated compounds which can be employed as starting materials in the dimerizations of this invention are diene, alkyne, and arene unsubstituted compounds.

Contemplated equivalents of the processes of this invention are dimerizations employing hydrogen atoms produced from a source other than excited mercury atoms, e.g., by passing hydrogen gas through very high voltage electrical field, e.g., produced by a Tesla coil, or by exposing molecular hydrogen to laser energy or to a stream of high energy electrons. Alternatively, such excited hydrogen atoms can be used to augment rather than replace the hydrogen atoms generated by the excited mercury atoms used for the conversion of the starting compound or compounds to radicals.

Without further elaboration, it is believed that one skilled in the art can, using the preceding description, use the present invention to its fullest extent. The following preferred specific embodiments are, therefore, to be construed as merely illustrative, and not limitative of the remainder of the disclosure in any way whatsoever.

EXAMPLES

In all the examples that follow, unless otherwise stated, a stream of hydrogen is passed into the substrate or substrates in a flask, which also contains a drop of mercury, at 0° to 100° and the resulting gaseous stream, which is saturated with starting compound or compounds and mercury vapor, is then passed into a photoreactor fitted with either 4 or 16 low-pressure 8 watt mercury lamps.

The hydrogen flow (1-50 m/min) is continued until all the substrate evaporates and is carried into the reactor. The condensed product, deposited in the collector vessel, is washed out with a suitable solvent, e.g., ether, and distilled. The ether and a trace of monomer which distills first and the reaction product is then collected, usually by distillation in vacuo or in a rotary evaporator under reduced pressure.

In the preceding text and the following examples, the temperatures are in degrees Celsius.

EXAMPLE 1

2,5-Dimethyl-2,5-hexanediol 3g of hexene-1 and 22g. of THF were passed into the reactor tube in a stream of $N_2$ as carrier gas for 18h. The crude product was washed with water/ether to separate the 1 gram of water-soluble THF dimer, viz., 1-(1-methylpentyl)tetrahydrofuran, which was formed. The organic phase was chromatographed on silica gel. Elution with 5% ether and 5% petroleum ether in cyclohexane yielded material which was shown by gas chromatography to contain 96% of a single product identified by $^1H$ and $^{13}C$ NMR as 2,5-Dimethyl-2,5-hexanediol.

EXAMPLE 2

2,5-dimethyl-2,5-octanediol

30 Gms. of tert-butanol were passed in a 30 ml/min flow of nitrous oxide carrier into the reactor tube while the tube was irradiated for 4.25 hours inside a photoreactor equipped with 16, 8-watt low pressure mercury lamps. During irradiation, a fan kept the temperature inside the quartz tube at an average of 50° C. The crude reaction mixture was evaporated under reduced pressure to give 0.65 g. of dimer fraction which was >95% 2,5-dimethyl-2,5-octanediol. 250 MHz $^{13}C$ NMR ($CDCl_3$) 70.62, 37.92, 29.36. $^1H$ NMR ($CDCl_3$) 1.92 (s, 2H), 1.56 (s, 4H), 1.22 (s, 12H).

EXAMPLE 3

5,6-Dimethyl-2,9-decanedione 25 g. of 1-hexene-5-one were passed in a 15 ml/min flow of hydrogen into the reactor tube while the tube was irradiated for 17.5 hours inside a photoreactor equipped with sixteen 8 W low pressure mercury lamps. During irradiation the temperature inside the quartz tube averaged 65.C. The crude reaction mixture was evaporated under reduced pressure to give 8.2 g. of involatile product containing the title compound, in about 70% yield. 250 MH$^Z$ $^{13}C$ NMR ($CDCl_3$) 208.4, 41.3, 36.5, 35.7, 29.3, 28.1, 26.2, 15.6, 13.6.

EXAMPLE 4

2,2-Dimethyl-2,3-butanedinitrile

Hydrogen (50 ml/min) was bubbled through a flask containing-methacrylonitrile at 35° C., and passed into the reactor tube. The flask was irradiated for 20.75 hours inside a photoreactor equipped with 16 8-watt low pressure mercury lamps. During irradiation the temperature inside the quartz reactor tube averaged 65 C. The product was washed out with methacrylonitrile and evaporated under reduced pressure to give 9.8 g. of involatile product containing the title compound in about 95% yield. 250 MHz $^{13}C$ NMR (acetone-$d_6$) 122.6, 40.0, 23.0.

EXAMPLE 5

2,3-Dimethyl-1,4-butanediamine Hydrogen (20 ml/min) was bubbled through a flask containing allyl amine at 0° C., and passed into the reactor tube. The flask was irradiated for 18 h. inside a photoreactor equipped with four 8-watt low pressure mercury lamps. During irradiation the temperature inside the quartz tube averaged 35° C. The product reduced pressure to give 2.7 g. of involatile product containing about 70% of the title compound. 250 MHz $^{13}C$ NMR (acetone-$d_6$) 45.4, 43.9, 38.0, 36.6, 13.6, 11.0.

EXAMPLE 6

2,2'-Bis(cyclooentanone)

20 g. of cyclopentanone were passed into the reactor tube with a 30 ml/min flow of hydrogen gas once and irradiated for 17.5 h. inside a photoreactor equipped with sixteen 8 W low pressure mercury lamps. During irradiation, the temperature inside the quartz tube averaged 75° C. The crude reaction mixture was evaporated under reduced pressure to give 3.1 g. of residue, and then distilled under reduced pressure to yield 2.1 g. of the title dimer. 90 MHz $^{13}C$ NMR (CDCCl$_3$) 219.00, 218.01, 48.53, 47.84, 37.54, 37.31, 26.17, 24.88, 20.30, 20.07.

EXAMPLE 7

5,6-dimethyldecane

A stream of hydrogen (30 ml/min) saturated with 1-hexene at room temperature was passed into the photoreactor and photolyzed for 32 hours at 40°. The crude product was distilled under reduced pressure yielding 13.7 g of hexane dimers, 72% of which were 5,6-dimethyldecane (by GC). 250 MHz $^{13}C$-NMR (CDCl$_3$; data for d,l and meso mixture): 14.16 (q, IC), 16.57 (q, 2C), 23.26 (t, 2C), 30.25 (t, IC), 30.30, (t, IC),34.89 (t, IC), 36.92 (d, IC), 37.86 (d, IC).

EXAMPLE 8

6,7-bis(difluoromethyl)perfluorododecane

A stream of hydrogen (30 ml/min) saturated with perfluoro-1-heptene was passed into the photoreactor and photolyzed for 25 hours. 5.7 g of crude product consisted of a mixture of dimers (GC-MS) whose major component (55%) was the title compound, which shows the characteristic CF$_2$H-CFRR' moiety by $^1H$-NMR (in d$^6$-acetone: 6.30 8;$J^1_{H\text{-}F}$=51.5 Hz, $J^2_{H\text{-}F}$=4.5 Hz).

EXAMPLE 9

3,3,4,4-tetramethylhexane-1,6-diol

A stream of $H_2$ (30 ml/min) saturated with 3-methyl-3-buten-1-ol at 70° was passed into the photoreactor and photolyzed for 22 h. The crude product was concentrated under reduced pressure and the title product precipitated from pentane, yielding 3.1 g. 250 MHz $^{13}$C-NMR (CDCl$_3$): 21.22 (q, 4C), 37.33 (s, 2C), 38.77 (t, 2C), 59.79 (t, 2C).

EXAMPLE 10

2,3-dimethyl-1,4-bis(trimethylsilyl) butane

A stream of $H_2$ (30 ml/min) saturated with allyltrimethylsilane was passed into the photoreactor and photolyzed for 38 h. at room temperature. The crude was distilled under reduced pressure to give 5.2 g of the title product. 250 MHz $^{13}$C-NMR (CDCl$_3$; data for d,l and meso mixture): −0.57 (q, 3C), −0.51 (q, 3C), 17.84 (q, IC), 18.97 (q, IC), 20.50 (t, IC), 22.21 (t, IC), 36.51 (d, IC), 36.66 (d, IC).

EXAMPLE 11

5,6-dimethyldeca-1,9-diene dioxide

A stream of Hz (30 ml/min) saturated with 5-epoxy-1-hexene was passed into the photoreactor and photolyzed for 39 h. at room temperature.' The reaction mixture was distilled under reduced pressure, affording 4.8 g of the title diepoxide. 250 MHz $^{13}$C-NMR (CDCl$_3$; data for mixture of stereosomers): 13.63 (q), 15.63 (q), 28.36 (t), 28.57 (t), 30.02 (t), 30.17 (t), 30.27 (t), 30.36 (t), 35.86 (d), 36.75 (d), 36.83 (d), 46.09 (t), 46.18 (t), 46.24 (t), 51.60 (d), 51.71 d), 51.77 (d).

EXAMPLE 12

2,3-dimethylsuccinic acid dimethyl ester

A stream of $H_2$ (30 ml/min) saturated with methyl acrylate was passed into the photoreactor and photolyzed for 12 h. at room temperature. The product mixture was evaporated in vacuo to give 1.2 g of the title hydrodimer. 250 MHz $^{13}$C-NMR (CDCl$_3$; data for d,l and meso mixture): 13.10 (q, IC), 14.37 (q, IC), 41.24 (d, IC), 42.15 (d, IC), 51.25 (q, 2C), 174.49 (s, 2C).

EXAMPLE 13

2,3-diethoxybutane

A stream of $H_2$ (30 ml/min) saturated with allylethylether was passed into the photoreactor and photolyzed for 36 hours at room temperature. The crude product was distilled under reduced pressure to give 17.7 g of the title material, identified by GC-MS and $^{13}$C-NMR.

EXAMPLE 14

2-(1-methylpentyl)-tetrahydrofuran 3 g of 1-hexene and 22 g of THF were passed into the reactor tube with a 30 ml/min flow of $N_2$. The reaction mixture was washed with 150 ml of 1:1 v/v water/ether to separate the 1 g. of water soluble THF dimer 2-(1-methyl-pentyl)-tetrahydrofuran which was formed. The organic phase was chromatographed on silica gel. Elution with 5% ether and 5% petroleum ether in cyclohexane to yield material which was shown to be 96% pure title compound by GC. 250 MHz $^{13}$C-NMR (CDCl$_3$; data for d,l for meso mixture): 13.88 (q, 2C), 14.84 (q, IC), 15.40 (q, IC), 22.73 (t, 2C), 25.65 (t, IC), 25.75 (t, IC), 28.39 (t, IC), 28.74 (t, IC), 29.00 (t, IC), 29.15 (t, IC), 32.54 (t, IC), 33.13 (t, IC), 37.66 (d, 2C), 67.52 (t, 2C), 83.60 (d, 2C).

EXAMPLE 15

3-cyclohehyl-3-methyl-1-butanol 3 g of 3-methyl-3-buten-1-ol and 4 g of cyclohexane were passed in a 30 ml/min stream of nitrogen, into the reactor, which was irradiated at 80°, over a 48 h period. The product was concentrated and the residue extracted into 150 ml. 1:1 v/v methanol/cyclohexane. The alcohol phase was separated and distilled under reduced pressure to yield 0.7 g of the title compound as product. 250 MHz $^{13}$C-NMR (CDCl$_3$): 24.66 (q, 2C), 26.42 (t, IC), 26.77 (t, 2C), 26.89 (t, 2C), 33.95 (s, IC), 42.22 (t, IC), 46.62 (d, IC), 58.59 (t, IC).

EXAMPLE 16

2,2'-Bioiperidine

52 Gms. of freshly distilled piperidine were passed in a 30 ml/min flow of hydrogen over a 24 hour period through a photoreactor as shown in the drawing, equipped with I6 8-watt low pressure mercury lamps. The crude condensate was evaporated, leaving 19 Gms. of 2,2'-bipiperidine. 90 MHz $^{13}$C NMR (CDCl$_3$) 61.56, 61.23, 47.06, 46.61, 28.92, 27.81, 26.70, 26.31, 24.61, 24.48.

3.5 Gms of this dimer were passed in a stream of hydrogen over CuCrO$_3$ catalyst at 400° C. One pass produced 2.5 Gms. 2,2'-bipyridyl. 250 MHz $^{13}$C NMR (Acetone-d&) 159.69, 152.91, 140.56, 127.59, 124.24.

EXAMPLE 17

2,3-dimethylsuccinic acid dimethyl ester 4.8 mL (4.4 g) of methyl propionate were evaporated into a hydrogen stream and photolyzed in the photoreactor for 12 hours at 45° C. 0.8 g of the title product were obtained. The product was identified by comparison with the authentic compound made by hydrodimerizing methyl acrylate, which produced 1.2 g (41% yield) of the title product after 12 h at 25° C. in the 4-lamp photoreactor. In this dimerization, it is the C—H$_\alpha$ to the —CO$_2$ carbon which was attacked, because it is 2°, rather than the attack occurring at the 1° Me group.

EXAMPLE 18

2,3-diacetoxybutane

A stream of hydrogen was used to transfer 5.3 mL (4.8 g) of ethyl acetate into the 16-lamp photoreactor. After irradiation for 20 h at 45° C., 1.8 g of the title product were obtained. The product was identified by comparison with the authentic compound made by hydrodimerizing vinyl acetate in the 4-lamp reactor at 25° C. to give 0.9 g of the product (52% yield) after the C—H$\alpha$ to the —CO$_2$ group.

EXAMPLE 19

Octane-4,5-diol

A hydrogen stream (30 ml/min) was saturated with n-butanol and Hg vapor and passed through the reactor vessel shown in the drawing under photolysis. After 18h, 3 g of dimers had collected which consisted of 87% dl and meso octane-4,5-diol and only 13% other diol isomers. In contrast, Brown and Crabtree, J. Amer. Chem. Soc. 1989, 111, 3000 report only 35% of the 4,5-diol when the reaction is carried out under the conditions of the '342 patent, i.e., in a refluxing reactor in the absence of hydrogen.

What is claimed is:

1. In a Group IIb photosensitized vapor phase dimerization of an organic compound in which a gaseous mixture of a Group IIB metal and the organic compound is irradiated in a reaction zone with a photosensitizing amount of radiant energy, the improvement wherein:

(i) a continuous stream of the gaseous mixture is passed as a vapor phase in a single pass through the reaction zone at a temperature at which the thus-produced dimer condenses immediately upon the formation thereof and remains condensed while exposed to the radiant energy and both the condensate and a residual vapor phase are concurrently removed from the reaction zone, thereby minimizing secondary reactions between the dimer and itself, the starting organic compound or any by-products of the dimerization reaction, and the starting gaseous mixture comprises an actuating amount of hydrogen and the organic compound is an ethylenically unsaturated compound selected from the group consisting of unsaturated nitriles, unsaturated esters, unsaturated ethers, unsaturated ketones, unsaturated epoxides, unsaturated silanes, unsaturated amines, unsaturated phosphines and fluorinated alkenes; and (ii) the starting gaseous mixture comprises hydrogen and two ethylenically unsaturated compounds selected from the group consisting of alkenes of at least six carbon atoms, unsaturated nitriles, unsaturated epoxides, unsaturated silanes, unsaturated amines, unsaturated phosphines, and fluorinated alkenes and a continuous stream of the gaseous mixture is passed in a single pass through the reaction zone at a temperature at which the thus-produced dimer condenses immediately upon the formation thereof and remains condensed while exposed to the radiant energy and residual vapor phase is concurrently removed from the reaction zone, thereby minimizing secondary reactions between the dimer and itself, the starting organic compound or any by-products of the dimerization reaction; or (iii) the gaseous mixture comprises nitrous oxide and the organic compound is a saturated compound with C—H bond strengths greater than 100 kcal/mol or a mixture of the saturated compound and an alkene; or (iv) the starting gaseous mixture comprises an activating amount of hydrogen and the dimerization is a dehydrodimerization or cross-dimerization of a saturated hydrocarbon bearing a functional group which inactivates the saturated hydrocarbon molecule to excited mercury atom mediated photosensitized dimerization or a cross dimerization thereof with an alkane.

2. The method according to claim (iv) of claim 1, wherein the organic compound is a member of the group consisting of carboxylic acids, esters, ethers, ketones, epoxides, silanes, amines, phosphines, partially fluorinated alkanes and mixtures thereof.

3. The method according to (i) of claim 1, wherein the organic compound is an unsaturated nitrile.

4. The method according to (i) of claim 1, wherein the organic compound is an unsaturated ester.

5. The method according to (i) of claim 1, wherein the organic compound is an unsaturated ether.

6. The method according to (i) of claim 1, wherein the organic compound is an unsaturated ketone.

7. The method according to (i) of claim 1, wherein the organic compound is an unsaturated epoxide.

8. The method according to (i) of claim 1, wherein the organic compound is an unsaturated silane.

9. The method according to (i) of claim 1, wherein the organic compound is an unsaturated amine.

10. The method according to (i) of claim 1, wherein the organic compound is an unsaturated phosphine.

11. The method according to (i) of claim 1, wherein the organic compound is a fluorinated alkene.

12. The method according to (ii) of claim 1, wherein the mole ratio of unsaturated compound or compounds in the starting gaseous mixture is from 0.01-100.

13. The method according to (ii) of claim 1, wherein the mole ratio of the unsaturated compounds in the starting gaseous mixture is adjusted to improve the yield of cross-dimers based on one of the unsaturated compounds by vapor pressure biasing.

14. The method according to (iii) of claim 1, wherein the dimerization is a dehydrodimerization of a saturated compound selected from the group consisting of alkanes, saturated esters, saturated ethers, saturated ketones, saturated epoxides, saturated silanes, saturated amines, saturated phosphines, and partially fluorinated alkanes.

15. The method according to (iii) of claim 1, wherein the dimerization is a cross-dimerization of the saturated compound and an alkene.

16. The method according to claim 15, wherein the saturated compound is selected from the group consisting of saturated acids, esters, saturated ethers, saturated ketones, saturated epoxides, saturated amines, saturated phosphines, and partially fluorinated alkanes.

17. The method according to (e) of claim 1, wherein the organic compound is a saturated alkane acid or ester.

18. The method according to (i) of claim 1, wherein the Group IIB metal is mercury and the frequency of the radiant energy is about 254 nm.

19. The method according to (ii) of claim 1, wherein the Group IIB metal is mercury and the frequency of the radiant energy is about 254 nm.

20. The method according to (iii) of claim 1, wherein the Group IIB metal is mercury and the frequency of the radiant energy is about 254 nm.

21. The method according to (iv) of claim 1, wherein the Group IIB metal is mercury and the frequency of the radiant energy is about 254 nm.

22. In a group IIb photosensitized vapor phase dimerization of an organic compound in which a gaseous mixture of a Group IIB metal and the organic compound is irradiated in a reaction zone with a photosensitizing amount of radiant energy, the improvement wherein a continuous stream of the gaseous mixture is passed as a vapor phase in a single pass through the reaction zone at a temperature at which the thus-produced dimer condenses immediately upon the formation thereof and remains condensed while exposed to the radiant energy and both the condensate and a residual vapor phase are concurrently removed from the reaction zone, thereby minimizing secondary reactions between the dimer and itself, the starting organic compound or any by-products of the dimerization reaction.

23. The method according to claim 22, wherein the Group IIB metal is mercury and the frequency of the radiant energy is about 254 nm.

* * * * *